United States Patent
Okada et al.

(10) Patent No.: US 7,097,751 B2
(45) Date of Patent: Aug. 29, 2006

(54) BASE SEQUENCE DETECTING ELECTRODE, BASE SEQUENCE DETECTING DEVICE AND BASE SEQUENCE DETECTING METHOD

(75) Inventors: Jun Okada, Kanagawa (JP); Koji Hashimoto, Kanagawa (JP); Masayoshi Takahashi, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 457 days.

(21) Appl. No.: 10/239,175

(22) PCT Filed: Aug. 28, 2002

(86) PCT No.: PCT/JP02/08671

§ 371 (c)(1),
(2), (4) Date: Sep. 25, 2002

(87) PCT Pub. No.: WO04/019024

PCT Pub. Date: Mar. 4, 2003

(65) Prior Publication Data

US 2005/0089447 A1    Apr. 28, 2005

(30) Foreign Application Priority Data

Aug. 23, 2002   (JP)   .............................. 2002-244018

(51) Int. Cl.
*G01N 27/327*   (2006.01)
*C12Q 1/68*   (2006.01)

(52) U.S. Cl. ..................... 204/403.01; 435/6

(58) Field of Classification Search ................ 204/402, 204/403.01, 412; 435/6, 7.1, 7.2
See application file for complete search history.

(56) References Cited

U.S. PATENT DOCUMENTS 4,874,500 A * 10/1989 Madou et al. ............... 204/412
6,203,981 B1 * 3/2001 Ackley et al. .................. 435/6
6,391,558 B1 * 5/2002 Henkens et al. ............... 435/6

FOREIGN PATENT DOCUMENTS

EP   1 065 278 A2   1/2001
EP   1 077 264      2/2001
EP   1 120 646      8/2001

(Continued)

OTHER PUBLICATIONS

H. Miyahara, et al., T. IEE Japan, vol. 121-E, No. 4, pp. 187-191, "Electrochemical Array (ECA) as an Integrated Multi-Electrode DNA Sensor", 2001.

(Continued)

*Primary Examiner*—Alex Noguerola
(74) *Attorney, Agent, or Firm*—Oblon, Spivak, McClelland, Maier & Neustadt, P.C.

(57) ABSTRACT

A conductive detecting electrode (2), first blocking molecules (21) formed so as to cover a surface of the detecting electrode (2), the first blocking molecules decreasing adsorption of an intercalating agent to the surface of the detecting electrode (2), a target-complementary probe (23) immobilized to the detecting electrode (2) via a spacer member (22) comprising straight chain organic molecules, the target-complementary probe including a base sequence complementary to a target base sequence which is an object of detection, a conductive comparison electrode (3), and second blocking molecules (31) formed so as to cover a surface of the comparison electrode (3), the second blocking molecules decreasing adsorption of an intercalating agent to the surface of the comparison electrode (3), are provided.

22 Claims, 11 Drawing Sheets

FOREIGN PATENT DOCUMENTS

| | | |
|---|---|---|
| EP | 1 136 570 A2 | 9/2001 |
| EP | 1 146 331 | 10/2001 |
| JP | 3076232 | 8/2000 |
| JP | 2001-296270 | 10/2001 |
| WO | WO 99/67425 | 12/1999 |
| WO | WO 00/32813 | 6/2000 |
| WO | 2002-195997 | 7/2002 |
| WO | WO 02/063041 A1 | 8/2002 |

OTHER PUBLICATIONS

S. O. Kelley, et al., Nucleic Acids Research, vol. 27, No. 24, pp. 4830-4837, "Single-Base Mismatch Detection Based on Charge Transduction Through DNA", 1999.

A. B. Steel, et al., Biophysical Journal, vol. 79, pp. 975-981, "Immobilization of Nucleic Acids at Solid Surfaces: Effect of Oligonucleotide Length on Layer Assembly", Aug. 2000.

A. B. Steel, et al., Analytical Chemistry, vol. 70, pp. 4670-4677, "Electrochemical Quantitation of DNA Immobilized on Gold", 1998.

* cited by examiner

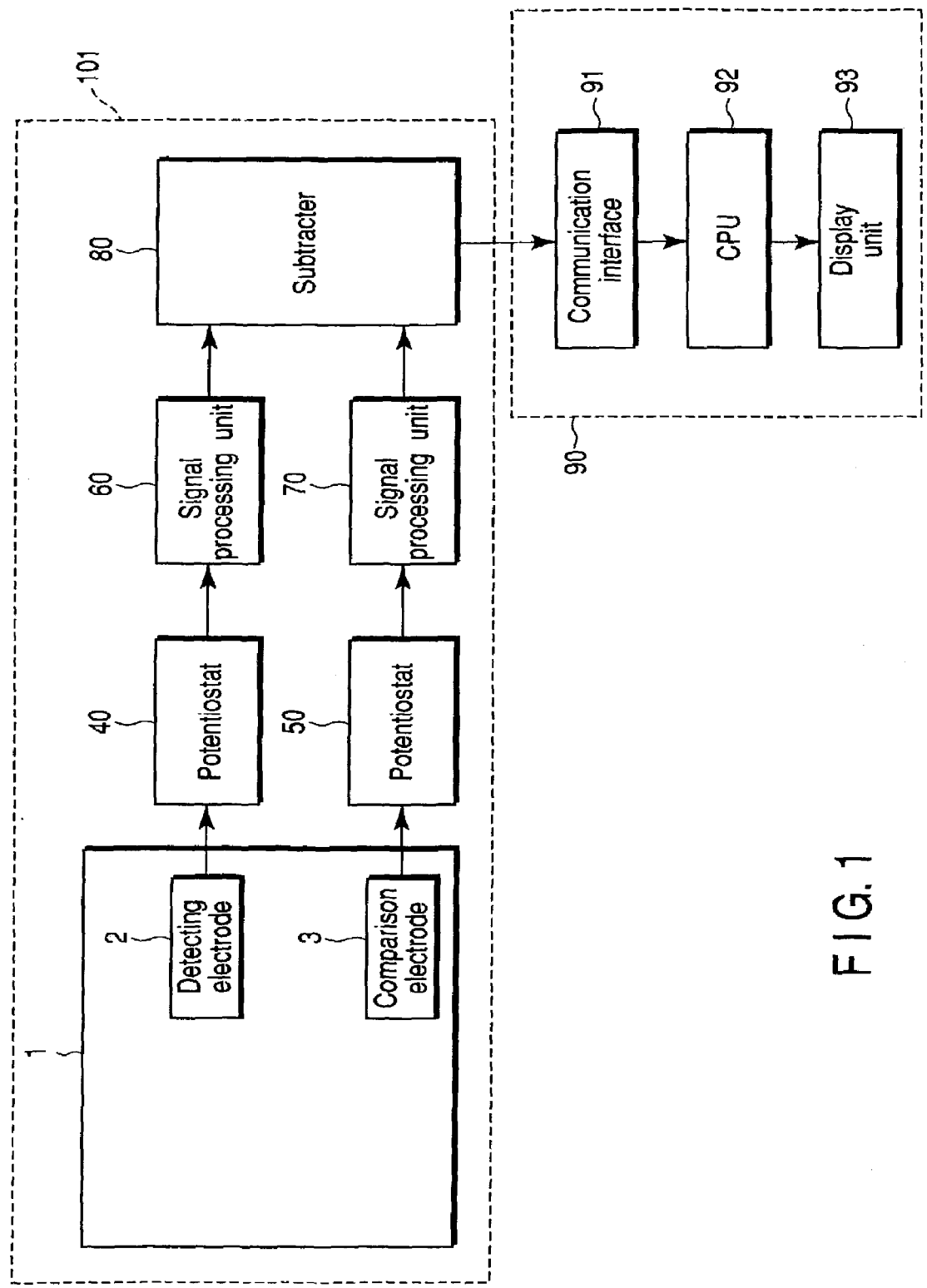
F I G. 1

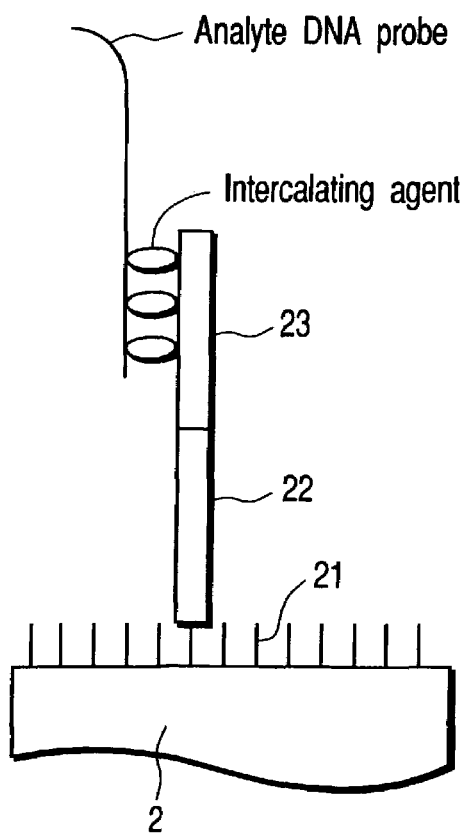
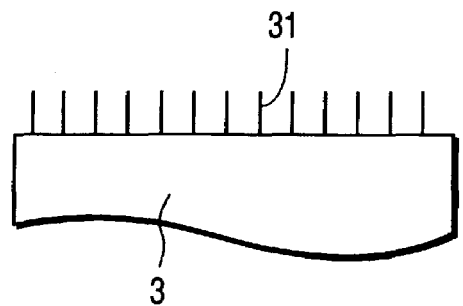
FIG. 2A  FIG. 2B
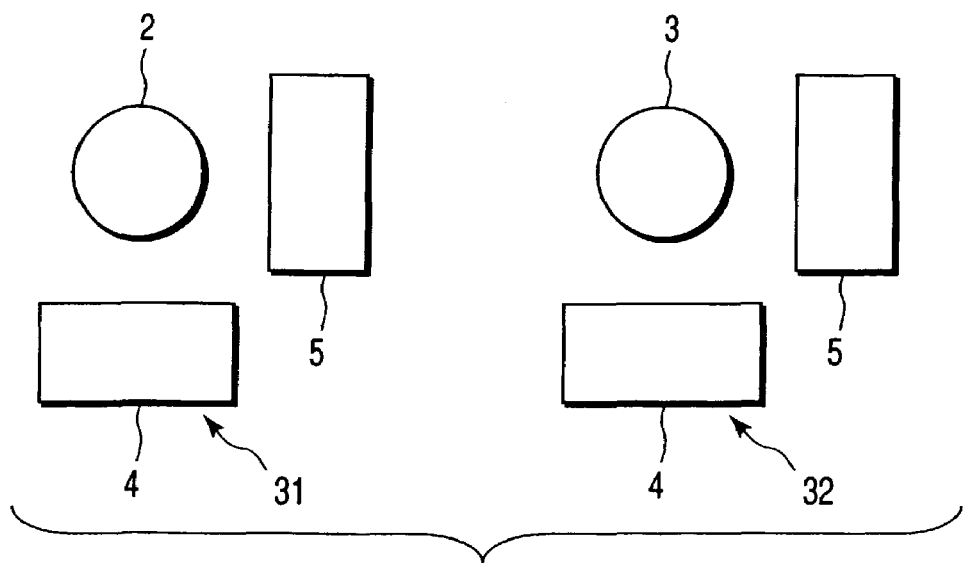
FIG. 3

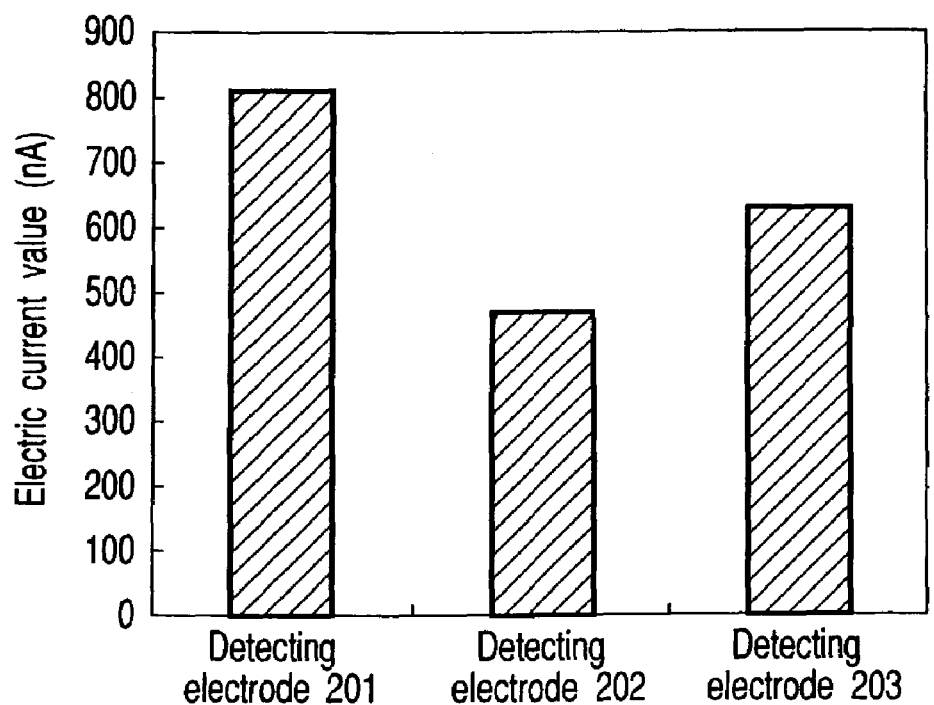
F I G. 17
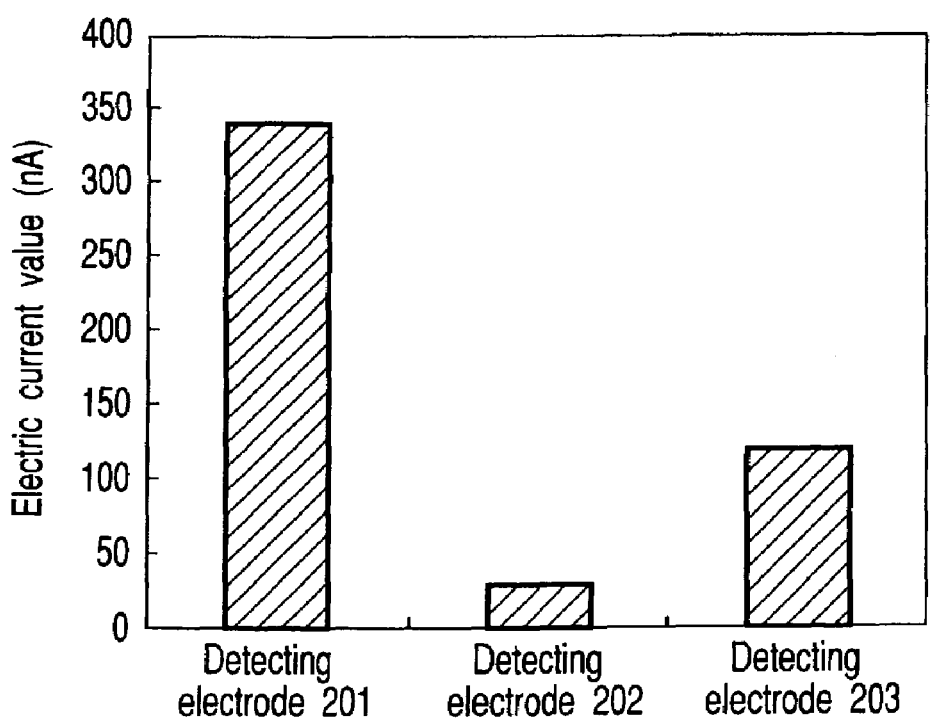
F I G. 18

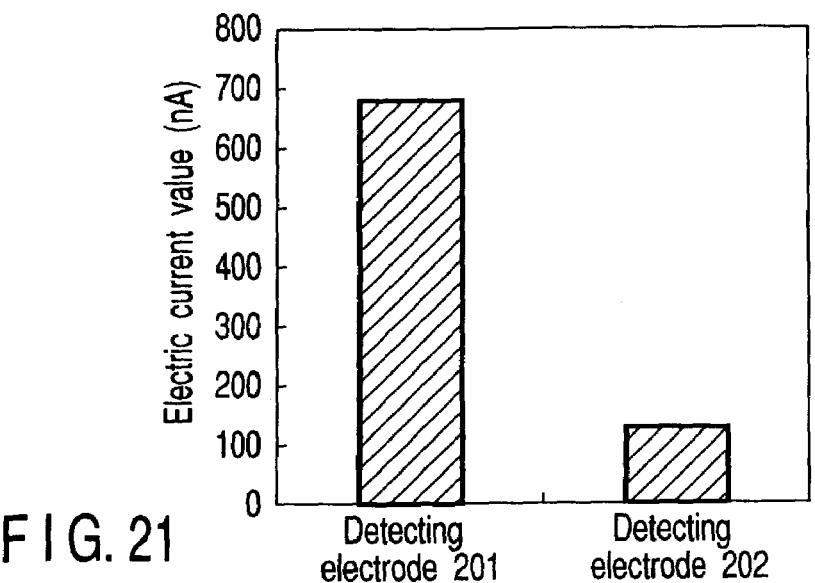
FIG. 21
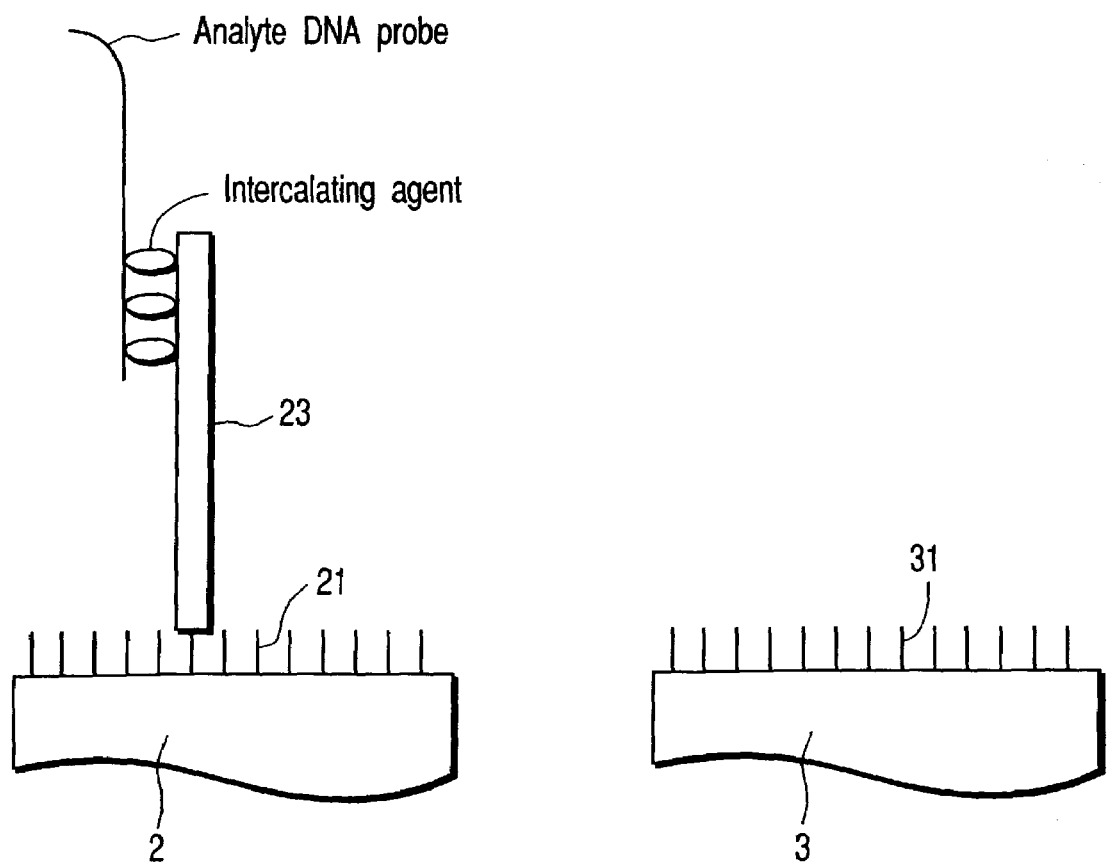
FIG. 22A
FIG. 22B

SEQUENCE LISTING

<160> NUMBER OF SEQ ID NOS: 5

<210> SEQ ID NO 1
<211> LENGTH: 121
<212> TYPE: DNA
<213> ORGANISM: Homo sapiens

<400> SEQUENCE: 1
ggcctccgct ctcgcttcgc ctctttcacc ccgcgcccag ccccgccccg cgccgcgaag        60
aaatgaaact cacagaccct gtgctgaggg cggctccggg cgcagaaacg aaacctagct       120
c                                                                      121

<210> SEQ ID NO 2
<211> LENGTH: 15
<212> TYPE: DNA
<213> ORGANISM: Homo sapiens

<400> SEQUENCE: 2
gtttctgcgc ccgga                                                        15

<210> SEQ ID NO 3
<211> LENGTH: 15
<212> TYPE: DNA
<213> ORGANISM: Homo sapiens

<400> SEQUENCE: 3
gtttctgcac ccgga                                                        15

<210> SEQ ID NO 4
<211> LENGTH: 15
<212> TYPE: DNA
<213> ORGANISM: Homo sapiens

<400> SEQUENCE: 4

```
gtttctgctc ccgga                                                      15

<210> SEQ ID NO 5
<211> LENGTH: 15
<212> TYPE: DNA
<213> ORGANISM: Escherichia coli

<400> SEQUENCE: 5
gacctgcttc tgact                                                      15
```

BASE SEQUENCE DETECTING ELECTRODE, BASE SEQUENCE DETECTING DEVICE AND BASE SEQUENCE DETECTING METHOD

CROSS-REFERENCE TO RELATED APPLICATIONS

The present application is a National Stage (371) of PCT/JP02/08671 filed on Aug. 28, 2002, which claims priority to JP 2002-244018, filed on Aug. 23, 2002.

TECHNICAL FIELD

The present invention relates to a base sequence detecting electrode, a base sequence detecting device and a base sequence detecting method for specifically detecting a specific gene existing in a sample.

BACKGROUND ART

Due to developments in genetic engineering in recent years, in the medical field, diagnosis and prevention of diseases by genes has come to be possible. Diagnosis by using genetic engineering is called gene diagnosis. In gene diagnosis, by detecting defect or change in a gene of a human, which may be source of a disease, diagnosis or measurement can be carried out before the onset of a disease or at the initial stage thereof. Further, by detecting a gene of a contracted virus or pathogenic bacteria, an accurate diagnosis is possible.

A general gene detecting method conventionally used is as follows.

First, a gene is extracted from a sample. If necessary, the gene is cut by appropriate restriction endonuclease, and thereafter, electrophoresis and Southern plotting are carried out. Next, a nuclease probe having a base sequence complementary to the target gene which is the object of detection is hybridized with the plotted gene. Note that the nuclease probe is usually labeled by a fluorescent dye. Then, the fluorescent dye is excited by laser light. Accordingly, the hybridized nuclease probe is detected, and the existence of the target gene is verified.

However, in this detecting method using a fluorescent dye, it takes at least a few days until detection of a gene. Further, the nuclease probe must be labeled by a high-priced fluorescent dye. In addition, a laser generating device for exciting the fluorescent dye is needed, and the device becomes large.

In order to solve the above-described problems of the detecting method using a fluorescent dye, a gene detecting method using an electrochemical method has been conceived of. The detecting method using an electrochemical method is disclosed in Japanese Patent No. 2573443 conceived of by the present inventors, and the contents thereof are incorporated herein by reference. In accordance with this electrochemical method, detecting an electrochemical signal from an electrode having a probe immobilized thereto allows existence of the target gene to be verified.

However, in gene detection using an electro-chemical method, background current arises at the time of current detection. Accordingly, current caused by derivation with the probe and the background current are included in the current value detected from the electrode. Therefore, from the results of detection, it has been difficult to extract only the current derived from the probe.

DISCLOSURE OF INVENTION

An object of the present invention is to provide a base sequence detecting electrode, a base sequence detecting device and a base sequence detecting method which precisely carry out detection of current based on an interaction with a target base sequence.

According to one aspect of the present invention, there is provided a base sequence detecting electrode comprising: a conductive detecting electrode; first blocking molecules formed so as to cover a surface of the detecting electrode, the first blocking molecules decreasing adsorption of an intercalating agent to the surface of the detecting electrode; a target-complementary probe immobilized to the detecting electrode, the target-complementary probe having a base sequence complementary to a target base sequence which is an object of detection; a conductive comparison electrode; and second blocking molecules formed so as to cover a surface of the comparison electrode, the second blocking molecules decreasing adsorption of an intercalating agent to the surface of the comparison electrode.

According to another aspect of the present invention, there is provided a base sequence detecting device comprising: a conductive detecting electrode; first blocking molecules formed so as to cover a surface of the detecting electrode, the first blocking molecules decreasing adsorption of an intercalating agent to the surface of the detecting electrode; a target-complementary probe immobilized to the detecting electrode, the target-complementary probe having a base sequence complementary to a target base sequence which is an object of detection; a conductive comparison electrode; second blocking molecules formed so as to cover a surface of the comparison electrode, the second blocking molecules decreasing adsorption of an intercalating agent to the surface of the comparison electrode; and a subtracter which subtracts an electrochemical signal detected at the comparison electrode from an electrochemical signal detected at the detecting electrode.

According to still another aspect of the present invention, there is provided a base sequence detecting method comprising: detecting electrochemical signals at a detecting electrode and a comparison electrode of a base sequence detecting device comprising: the conductive detecting electrode; first blocking molecules formed so as to cover a surface of the detecting electrode, the first blocking molecules decreasing adsorption of an intercalating agent to the surface of the detecting electrode; a target-complementary probe immobilized to the detecting electrode via a first spacer member comprising straight chain organic molecules, the target-complementary probe having a base sequence complementary to a target base sequence which is an object of detection; the conductive comparison electrode; and second blocking molecules formed so as to cover a surface of the comparison electrode, the second blocking molecules decreasing adsorption of an intercalating agent to the surface of the comparison electrode; and subtracting an electrochemical signal detected at the comparison electrode from an electrochemical signal detected at the detecting electrode.

BRIEF DESCRIPTION OF DRAWINGS

FIG. 1 is a block diagram showing a concept of an entire structure of a base sequence detecting device according to an embodiment of the present invention.

FIG. 2A and FIG. 2B are diagrams showing detailed structures of a detecting electrode and a comparison electrode according to the embodiment.

FIG. 3 is a top view of an electrode structure including the detecting electrode and the comparison electrode according to the embodiment.

FIG. 17 is a graph showing results of current measurement of a conventional base sequence detecting device.

FIG. 18 is a graph showing results of current measurement of the base sequence detecting device including the comparison electrode.

FIG. 21 is a graph showing results of current measurement of a base sequence detecting device in which straight chain alkane molecules are used as a spacer member.

FIG. 22A and FIG. 22B are diagrams showing a modified example in which a target nuclease probe is immobilized without using a spacer member.

BEST MODE FOR CARRYING OUT OF THE INVENTION

Figure 4:
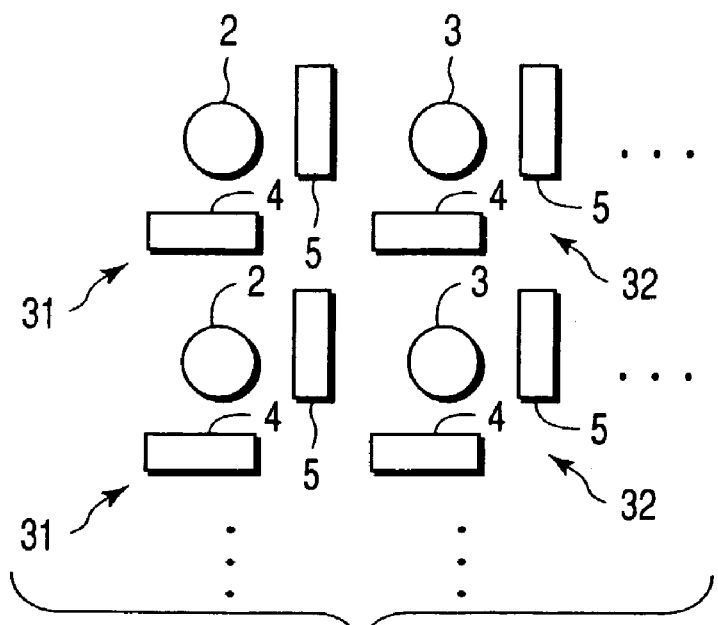
FIG. 4 is a top view of an electrode structure including the detecting electrode and the comparison electrode according to the embodiment.

Hereinafter, embodiments of the present invention will be described with reference to the figures.

FIG. 1 is a block diagram showing a concept of an entire structure of a base sequence detecting device according to an embodiment of the present invention. As shown in FIG. 1, a detecting electrode 2 and a comparison electrode 3 are disposed in an electrochemical cell 1. Electric current at the detecting electrode 2 and comparison electrode 3 are respectively detected at potentiostats 40 and 50. The obtained electrochemical signals are respectively outputted to signal processing units 60 and 70. The signal processing units 60 and 70 carry out a signal processing such as calculation of a peak current value or the like, and output the signal-processed data to a subtracter 80.

The subtracter 80 subtracts the data obtained from the signal processing unit 70 from the data obtained from the signal processing unit 60, and outputs the results of subtraction to a computer 90.

The electrochemical cell 1, the detecting electrode 2, the comparison electrode 3, and the potentiostats 40 and 50 are formed in and/or on a semiconductor substrate 101 (chip) for detecting a base sequence. Further, the detecting electrode 2, the comparison electrode 3, and the potentiostats 40 and 50 are comprised of an integrated circuit of the semiconductor chip. The subtracter 80 may be realized as an integrated circuit formed in and/or on the semiconductor substrate 101, or may be realized by a computer or a subtracter provided separately from the semiconductor substrate 101. The subtracter 80 may be realized by a computer and software controlling the computer, or may be realized as firmware in which the subtraction processing contents are recorded on a ROM or the like, or may be realized by only hardware.

The computer 90 may be any of computers which enable general arithmetic processing, for example, a personal computer or the like. The computer 90 comprises a communication interface 91, a CPU 92, and a display device 93. The communication interface 91 receives the results of subtraction from the subtracter 80, and outputs them to the CPU 92. The CPU 92 displays the results of subtraction on the display device 93.

FIG. 2A and FIG. 2B are diagrams showing detailed structures of the detecting electrode 2 and the comparison electrode 3. FIG. 2A shows the details of the detecting electrode 2, and FIG. 2B shows the details of the comparison electrode 3.

As shown in FIG. 2A, blocking molecules 21 are formed so as to cover the surface of the detecting electrode 2. The blocking molecule 21 is comprised of a molecule whose adsorption of an intercalating agent per unit area is less than that at the surface of the detecting electrode 2. Specifically, the blocking molecule 21 is comprised of, for example, mercapto hexanol, mercapto octanol, or the like. It is possible for the detecting electrode 2 to not be completely covered, and it suffices that at least one portion of the surface of the detecting electrode 2 is covered. In this way, by making a structure such that the blocking molecules 21 cover the surface of the detecting electrode 2, adsorption of the intercalating agent molecules to the surface of the detecting electrode 2 can be decreased.

The blocking molecule 21 is not particularly limited to the above-described materials. However, for example, straight chain alkane, alkene, alkyne, ether, ester, and ketones are preferable, and further, the blocking molecule 21 may be a molecule in which a plurality of these molecules are connected in a chain via atoms such as oxygen, nitrogen, sulphur, or the like. Further, molecules, in which a group which, among, for example, an alkyl group, a hydroxyl group, a carboxyl group, a sulfonic group, a nitro group, a phenyl group, an amino group, a thiol group, a halogen, and the like, is hard to interact with the intercalating agent molecules is introduced as a functional group, are more preferable. Further, it is preferable that these blocking molecules 21 are made to adsorb to the surface of the detecting electrode 2 via a thiol group, an amino group, or the like, and self-organizing monomolecular film is prepared. Other than this, an inorganic oxide layer, a macro-molecular layer, or the like may be formed.

Further, an end of a spacer member 22 is immobilized to the surface of the detecting electrode 2 on which the blocking molecules 21 are not formed. The spacer member 22 is formed from a material in which adsorption of the intercalating agent per unit area is less than that of the surface of the detecting electrode 2. Specifically, the spacer member 22 is comprised of straight chain organic molecules, and for example, ethylene glycol is appropriate. The material of the spacer member 22 is not particularly limited. However, for example, straight chain alkane, alkene, alkyne, ether, ester, and ketones are preferable. Further, the spacer member 22 may be a molecule in which a plurality of these molecules are connected in a chain via atoms such as oxygen, nitrogen, sulphur, or the like.

Moreover, a target-complementary nucleic acid probe 23 is immobilized to the other end of the spacer member 22. The target-complementary nucleic acid probe 23 is a probe comprising a nucleic acid having a base sequence complementary to the target nucleic acid sequence which is the object of detection. Thus, by using a structure in which the target-complementary nucleic acid probe 23 is immobilized to the detecting electrode 2 via the spacer member 22, the efficiency of the binding of the sample and the target-complementary nucleic acid probe 23 can be improved.

Conventionally, the intercalating agent molecules interact with the spacer member, and it is a cause of increasing the background current. However, as in the present embodiment, by selecting molecules, which it is hard for the intercalating agent molecules to interact with, as the structure of the spacer member 22, the background current can be decreased. The background current indicates current which is a cause of noise or the like other than the current caused by interaction between the target-complementary nucleic acid probe 23 disposed at the detecting electrode 2 and the intercalating agent. The background current includes current caused by, for example, interaction between the surface of the detecting electrode 2 and the intercalating agent, interaction between the blocking molecules 21 and the intercalating agent, and interaction between the spacer member 22 and the intercalating agent. The current caused by interaction between the target-complementary nucleic acid probe 23 and the intercalating agent is called probe current.

When the target-complementary nucleic acid probe 23 comprising straight chain organic molecules as described above is used, the background current is substantially only a current caused by the intercalating agent interacting with the surface of the detecting electrode 2. Therefore, the comparison electrode 3 to be described later may be comprised of only a blocking molecule layer, and it is extremely desirable. As a spacer molecule having such an effect, for example, there is a straight chain molecule to which one or a plurality of ethylene glycol are linked. Other than this, provided that the spacer molecule is a molecule which does not interact with the intercalating agent molecule, the material thereof is not limited.

As shown in FIG. 2B, at the comparison electrode 3, blocking molecules 31 are formed so as to cover the surface of the comparison electrode 3. The blocking molecule 31 is preferably comprised of the same material as that of the blocking molecules 21 covering the surface of the detecting electrode 2. However, it is not limited to that as far as it is a molecule exhibiting similar properties. The blocking molecule 31 may not completely cover the comparison electrode 3, and it suffices for at least one portion of the surface of the comparison electrode 3 to be covered. Thus, by using a structure in which the surface of the comparison electrode 3 is covered with the blocking molecules 31 whose material is the same as that of the blocking molecules 21, adsorption of the intercalating agent molecules to the surface of the detecting electrode 2 can be decreased, and the effect of reducing the effects with respect to the background currents at the detecting electrode 2 and the comparison electrode 3 can be the same.

FIG. 3 to FIG. 14 are schematic top views of electrode structures including the detecting electrode 2 and the comparison electrode 3. As shown in FIG. 3 to FIG. 14, as the types of electrodes, there are a counter electrode 4 and a reference electrode 5, in addition to the detecting electrode 2 and the comparison electrode 3. These detecting electrode 2, comparison electrode 3, counter electrode 4, and reference electrode 5 are formed from conductive materials, and these electrodes 2 to 5 are disposed in the electrochemical cell 1. A sample having an analyte base sequence for carrying out hybridization between the probes immobilized to the detecting electrode 2 and the comparison electrode 3, an intercalating agent, a buffer, and the like are filled in the electrochemical cell 1 in which these detecting electrode 2, comparison electrode 3, counter electrode 4, and reference electrode 5 are disposed, and electrochemical reaction is carried out therein.

The detecting electrode 2 and the comparison electrode 3 are electrodes for detecting the reaction current in the cell 1.

A DNA probe having a target-complementary base sequence which is complimentary to the target base sequence is immobilized to the detecting electrode 2. Probe current caused by interaction between the target-complementary nucleic acid probe and the intercalating agent is detected from the detecting electrode 2.

Figure 16:
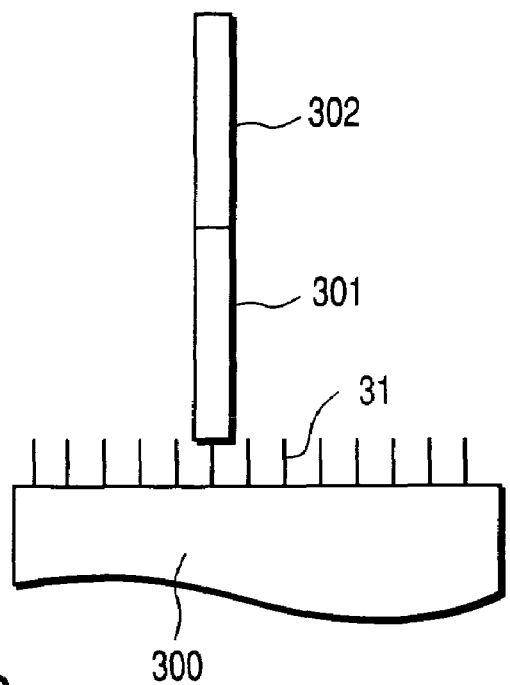
FIG. 16 is a diagram showing a modified example of the comparison electrode of the base sequence detecting device according to the embodiment.

The comparison electrode 3 is an electrode which detects background current such as noise or the like, and thereafter, decreases the effects of the noise or the like by subtracting the background current from the current detected at the detecting electrode 2. The comparison electrode 3 is used without the probe being not fixed, or is used with a dummy probe being immobilized as shown in FIG. 16 described later.

The counter electrode 4 is an electrode supplying electric current to the inside of the cell 1 by applying a predetermined voltage between the detecting electrode 2 or the comparison electrode 3.

The reference electrode 5 is an electrode which negatively feeds back the electrode voltage to the counter electrode 4 in order to control the voltage between the reference electrode 5 and the detecting electrode 2, or the reference electrode 5 and the comparison electrode 3, to a predetermined voltage characteristic. The voltage by the counter electrode 4 is controlled by the reference electrode 5, and oxidation current detection, which does not depend on various types of detecting conditions in the cell 1 and is highly accurate, can be carried out.

FIG. 3 shows a detecting electrode side 3-electrode system 31 comprising the detecting electrode 2, the counter electrode 4, and the reference electrode 5, and a comparison electrode side 3-electrode system 32 comprising the counter electrode 3, the counter electrode 4, and the reference electrode 5.

At the detecting electrode side 3-electrode system 31, the rectangular counter electrodes 4, which have a longitudinal direction in a predetermined direction, are disposed at predetermined intervals with respect to the circular detecting electrodes 2. Further, the rectangular reference electrodes 5, which have a longitudinal direction in a direction substantially perpendicular to the longitudinal direction of the counter electrodes 4, are disposed at predetermined intervals with respect to the detecting electrodes 2. An example is shown in which the electrodes are disposed such that the distance between the detecting electrode 2 and the counter electrode 4 and the distance between the detecting electrode 2 and the reference electrode 5 are substantially the same. However, it is not limited to this example, and the elements may be disposed at different distances.

The comparison electrode side 3-electrode system 32 is configured such that the detecting electrode 2 of the detecting electrode side 3-electrode system 31 is replaced with the comparison electrode 3. These 3-electrode systems 31 and 32 are made to be an electrode system of one set, and the potentiostats 40 and 50 are connected thereto.

FIG. 4 is a more specific electrode structural example configured on the basis of the electrode structure of FIG. 3. As shown in FIG. 4, the 3-electrode systems 31 and 32, which are the same as those shown in FIG. 3, are alternately disposed in a matrix manner. In FIG. 4, an example in which the same 3-electrode systems are aligned in a column direction and different 3-electrode systems are alternately aligned in a row direction is shown. However, the same 3-electrode systems may be aligned in the row direction, and different 3-electrode systems may be alternately aligned in the column direction. Further, different 3-electrode systems may be alternately aligned in both the row and column directions. In this case, the common 3-electrode systems are disposed so as to be aligned in oblique directions of the matrix.

Figure 5:
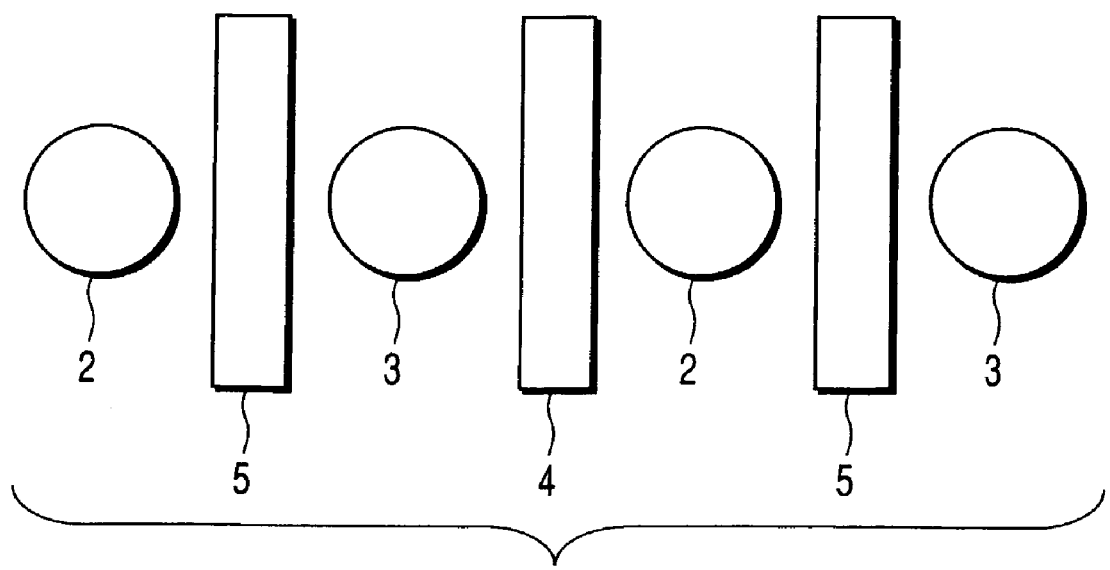
FIG. 5 is a top view of an electrode structure including the detecting electrode and the comparison electrode according to the embodiment.

FIG. 5 shows another arrangement example of electrodes having the same shape as in FIG. 3. The reference electrodes 5, whose longitudinal directions are the same as those of the rectangular counter electrodes 4, are disposed at equal intervals so as to sandwich the counter electrodes 4. The comparison electrodes 3 are disposed between the counter electrode 4 and one reference electrode 5, and further, the detecting electrodes 2 are disposed at the side of the reference electrode 5 opposite to the side at which the comparison electrodes 3 are provided. Further, the detecting electrodes 2 are disposed between the counter electrodes 3 and the other reference electrode 5, and further, the comparison electrodes 3 are disposed at the side of the reference electrode 5 opposite to the side at which the comparison electrodes 3 are provided. The distance between the counter electrode 4 or the reference electrode 5 and the detecting electrodes 2 or the comparison electrodes 3 are equal intervals. Further, the detecting electrodes 2 and the comparison electrodes 3 are disposed at positions which are symmetrical across the reference electrode 5. Moreover, the detecting electrodes 2 and the comparison electrodes 3 are disposed at positions symmetrical across the counter electrode 4 so as to sandwich the counter electrode 4.

Figure 6:
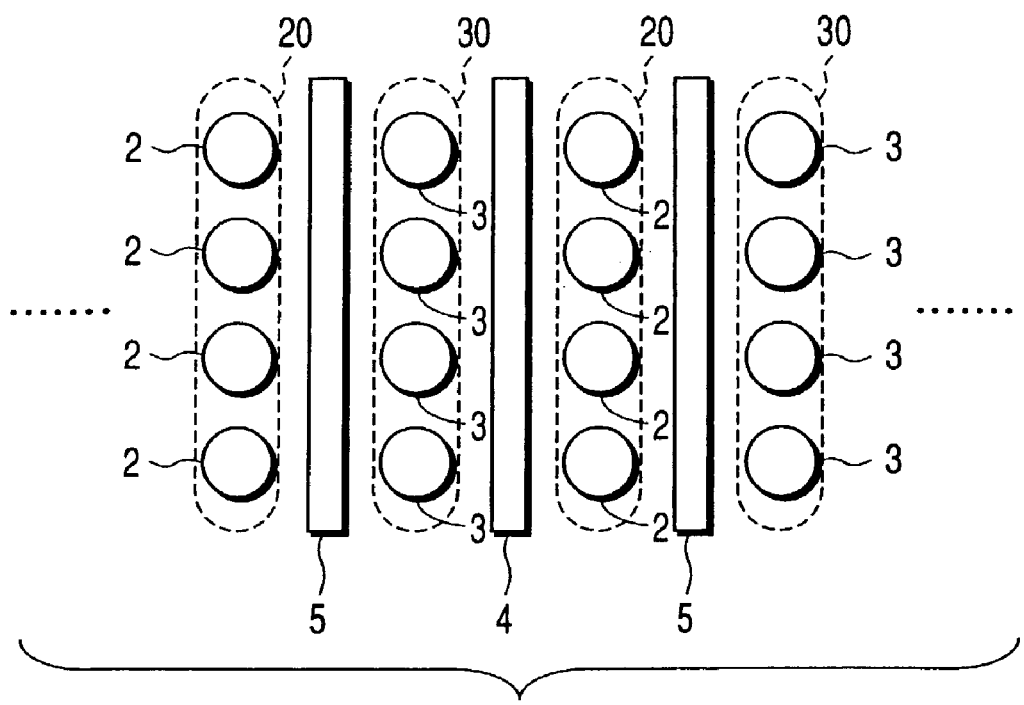
FIG. 6 is a top view of an electrode structure including the detecting electrode and the comparison electrode according to the embodiment.

FIG. 6 is a more specific electrode structural example configured on the basis of the electrode structure of FIG. 5. As shown in FIG. 6, it has a similar electrode structure as that shown in FIG. 5. However, a plurality of the detecting electrodes 2 and the comparison electrodes 3 are disposed at equal intervals along the longitudinal directions of the counter electrode 4 and the reference electrodes 5, and they respectively form detecting electrode groups 20 and comparison electrode groups 3. Further, the detecting electrodes 2 and the comparison electrodes 3 are disposed at positions symmetrical across the reference electrodes 5 or the counter electrodes 4. The detecting electrodes 2 and the comparison electrodes 3 disposed at symmetrical positions are electrodes which are objects of subtraction. Namely, the 3-electrode system is comprised of the detecting electrodes 2 or the comparison electrodes 3 disposed at the positions symmetrical with respect to the reference electrode 5, and the reference electrode 5, and further, the counter electrode 4 provided so as to be near to the detecting electrodes 2 or the comparison electrodes 3. The distances from each detecting electrode 2 to the counter electrode 4 and the reference electrode 5 are equal, and the distances from each comparison electrode 3 to the counter electrode 4 and the reference electrode 5 are equal. The potentiostat 40 or 50 is connected to the 3-electrode system. A plurality of electrode sets, which are comprised of one detecting electrode group 20, one comparison electrode group 30, one counter electrode 4, and one reference electrode 5, are disposed in a direction different from the longitudinal direction of these electrodes or electrode groups (preferably the substantially perpendicular direction).

Figure 7:
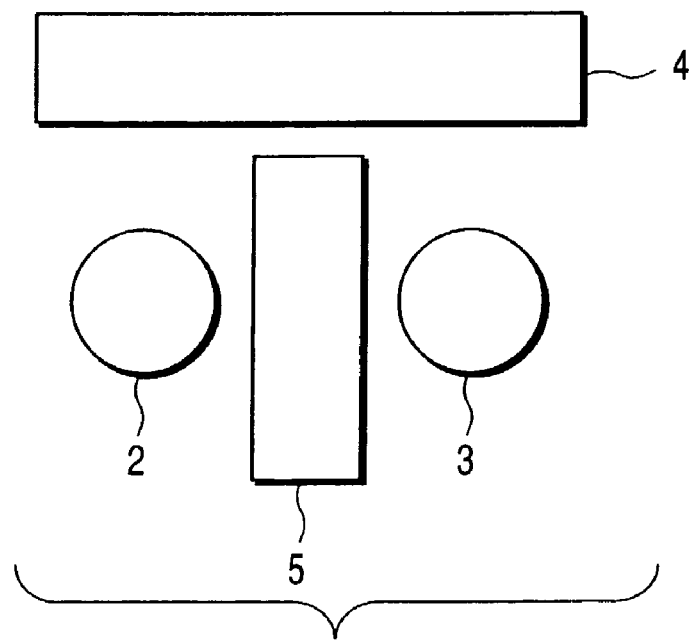
FIG. 7 is a top view of an electrode structure including the detecting electrode and the comparison electrode according to the embodiment.

FIG. 7 shows another arrangement example of electrodes having the same shape as in FIG. 3 and FIG. 5. The reference electrode 5 is disposed at a predetermined interval from the vicinity of the center of the counter electrode 4 and such that the longitudinal direction thereof is substantially perpendicular to the counter electrode 4. The detecting electrode 2 is disposed at a predetermined interval from the reference electrode 5, and the comparison electrode 3 is disposed at a position symmetrical to the detecting electrode 2 with respect to the reference electrode 5.

Figure 8:
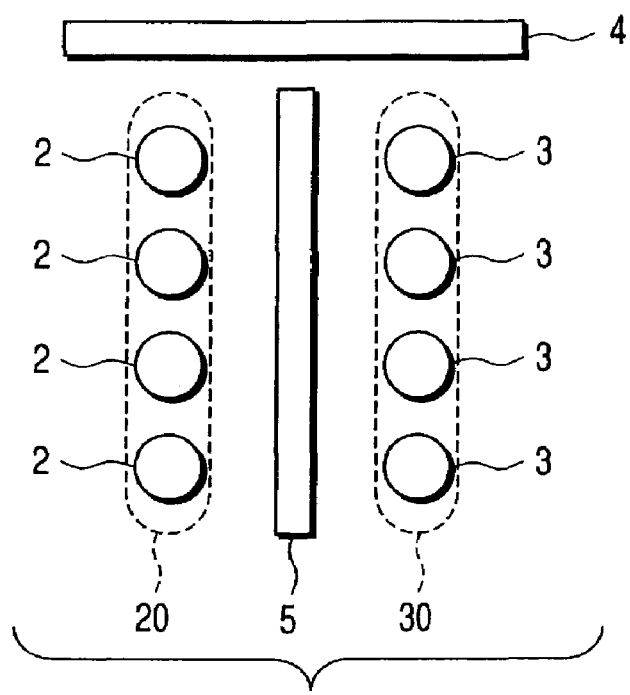
FIG. 8 is a top view of an electrode structure including the detecting electrode and the comparison electrode according to the embodiment.

FIG. 8 is a more specific electrode structural example configured on the basis of the electrode structure of FIG. 7. As shown in FIG. 8, it has a similar electrode structure as that shown in FIG. 7. A plurality of the detecting electrodes 2 and the comparison electrodes 3 are disposed at positions which are symmetrical across the reference electrode 5 at a equal intervals along the longitudinal directions of the reference electrode 5, and respectively form the detecting electrode group 20 and the comparison electrode group 30. The detecting electrodes 2 and the comparison electrodes 3 disposed at symmetrical positions with respect to the reference electrode 5 are electrodes which are objects of subtraction. Namely, the 3-electrode system is comprised of the detecting electrodes 2 or the comparison electrodes 3 disposed at positions symmetrical with respect to the reference electrode 5, and the reference electrode 5, and further, the counter electrode 4 provided so as to be perpendicular to the reference electrode 5. The potentiostat 40 or 50 is connected to the 3-electrode system. The distances from each detecting electrode 2 to the reference electrode 5 are equal, and the distances from each comparison electrode 3 to the reference electrode 5 are equal.

Figure 9:
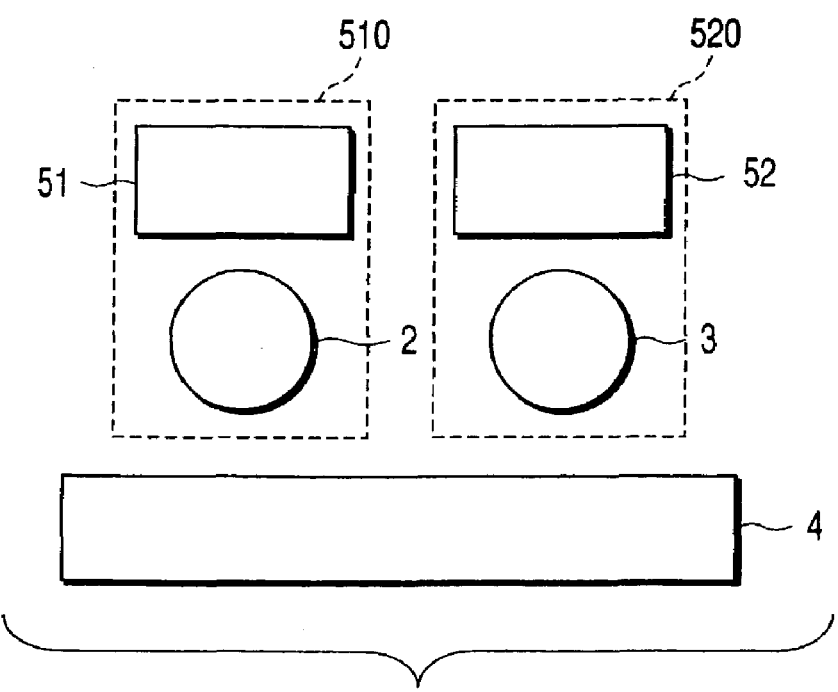
FIG. 9 is a top view of an electrode structure including the detecting electrode and the comparison electrode according to the embodiment.

FIG. 9 shows an other arrangement example of electrodes having the same shape as in FIGS. 3, 5 and 7. Reference electrodes 51, 52, which have longitudinal directions substantially parallel to the longitudinal direction of the counter electrode 4, are disposed at predetermined intervals from the counter electrode 4. The detecting electrode 2 is disposed between the one reference electrode 51 and the counter electrode 4, and the comparison electrode 3 is disposed between the other reference electrode 52 and the counter electrode 4. The positional relationship of the reference electrode 51 for the detecting electrode 2 with respect to the counter electrode 4, and the positional relationship of the reference electrode 52 for the comparison electrode 3 with respect to the counter electrode 4 are equal. A set of the detecting electrode 2 and the reference electrode 51 provided in correspondence with the detecting electrode 2 is called a detecting electrode side electrode group 510, and a set of the comparison electrode 3 and the reference electrode 52 provided in correspondence with the comparison electrode 3 is called a comparison electrode side electrode group 520. A 3-electrode system is comprised of one detecting electrode side electrode group 510 and the counter electrode 4, and the potentiostat 40 is connected thereto. A 3-electrode system is comprised of one comparison electrode side electrode group 520 and the counter electrode 4, and the potentiostat 50 is connected thereto.

Figure 10:
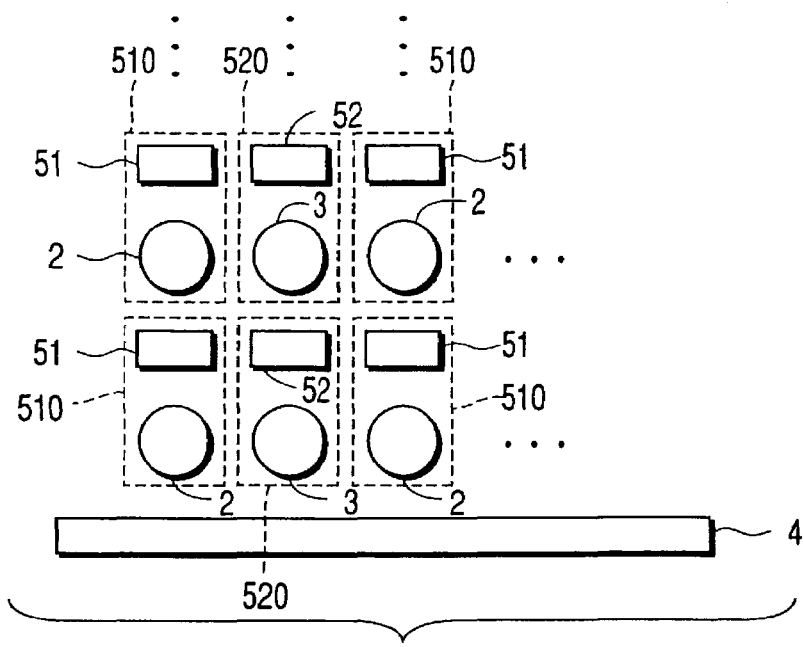
FIG. 10 is a top view of an electrode structure including the detecting electrode and the comparison electrode according to the embodiment.

FIG. 10 is a more specific electrode structural example configured on the basis of the electrode structure of FIG. 9. As shown in FIG. 10, it has a similar electrode structure as that shown in FIG. 9. It is a matrix structure in which a plurality of the detecting electrode side electrode groups 510 are disposed in the column direction at equal intervals, and a plurality of the comparison electrode side electrode groups 520 are disposed in the row direction at equal intervals, and the both electrode groups are alternately disposed in the row direction. The 3-electrode system is comprised of each of electrode groups 510, 520, and the counter electrode 4, and the potentiostat 40 or 50 is connected thereto. Note that an example is shown in which the same electrode groups are disposed in the column direction. However, it may be a structure in which the detecting electrode side electrode groups 510 and the comparison electrode side electrode groups 520 are alternately disposed in the column direction as well. Further, a case is shown in which the row direction and the column direction are substantially perpendicular to each other. However, it is not limited to this, and the column direction may have an angle which is not perpendicular to the row direction.

Figure 11:
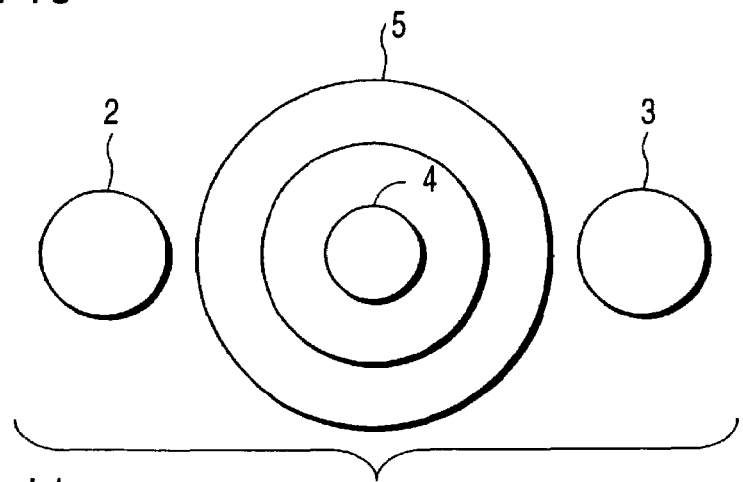
FIG. 11 is a top view of an electrode structure including the detecting electrode and the comparison electrode according to the embodiment.

FIG. 11 is a diagram showing an example of an electrode structure configured of the detecting electrode 2 and the comparison electrode 3 having the same shape as in FIGS. 3, 5, 7, and 9, and the circular counter electrode 4 and the ring-shape reference electrode 5. As shown in FIG. 11, the ring-shape reference electrode 5 having the same the center as the circular counter electrode 4 is disposed so as to surround the counter electrode 4. Moreover, the detecting electrode 2 and the comparison electrode 3 are disposed at positions symmetrical with respect to the counter electrode 4 and at a predetermined interval from the outer periphery of the reference electrode 5.

Figure 12:
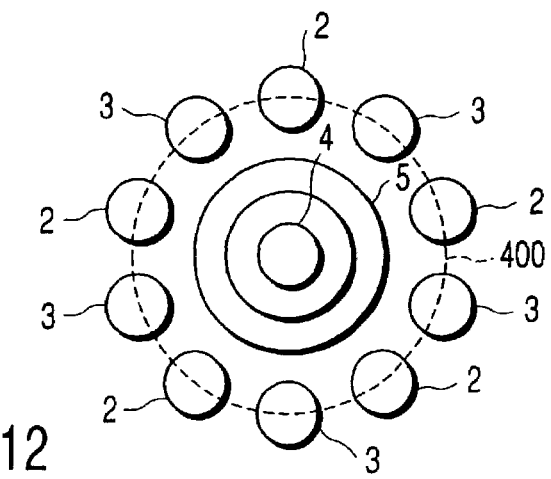
FIG. 12 is a top view of an electrode structure including the detecting electrode and the comparison electrode according to the embodiment.

FIG. 12 is a more specific electrode structural example configured on the basis of the electrode structure of FIG. 11. As shown in FIG. 12, it has a similar electrode structure as that shown in FIG. 11, and a plurality of the detecting electrodes 2 and a plurality of the comparison electrodes 3 are disposed at positions symmetrical with respect to the counter electrode 4. Further, because each of the plurality of detecting electrodes 2 and each of the plurality of detecting electrodes 2 are disposed at the same position from the counter electrode 4, it is configured such that the plurality of detecting electrodes 2 and counter electrodes 3 are alternately disposed on a circumference 400 whose center is the counter electrode 4. Both of the detecting electrode 2 and the comparison electrode 3 disposed at the positions symmetrical with respect to the counter electrode 4 may be objects of subtraction, or both of the detecting electrode 2 and the comparison electrode 3 which are adjacent to each other may be objects of subtraction.

Figure 13:
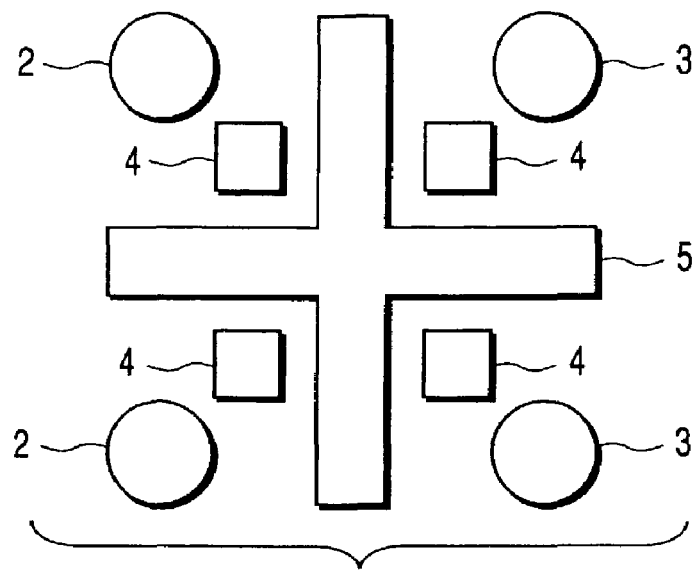
FIG. 13 is a top view of an electrode structure including the detecting electrode and the comparison electrode according to the embodiment.

FIG. 13 is a diagram showing an example of an electrode structure configured of the detecting electrodes 2 and the comparison electrodes 3 having the same shape as in FIGS. 3, 5, 7, and 9, and the square counter electrode 4 and the cross-shaped reference electrode 5. As shown in FIG. 13, the cross-shaped reference electrode 5, which is configured such that two rectangular electrodes whose longitudinal directions substantially perpendicularly intersect each other overlap, is disposed. At each of the four regions partitioned by the cross of the reference electrode 5, one of the counter electrodes 4 is disposed at a predetermined interval from the reference electrode 5. Further, at two regions among these four regions, one detecting electrode 2 is disposed respectively, and one comparison electrode 3 is disposed at the other two regions respectively. These detecting electrodes 2 and comparison electrodes 3 are disposed at positions further apart from the reference electrode 5 than the counter electrodes 4. The distances from the reference electrode 5 to the respective counter electrodes 4 are equal, and the distances from the reference electrode 5 to the respective detecting electrodes 2 and the respective comparison electrodes 3 are equal.

Figure 14:
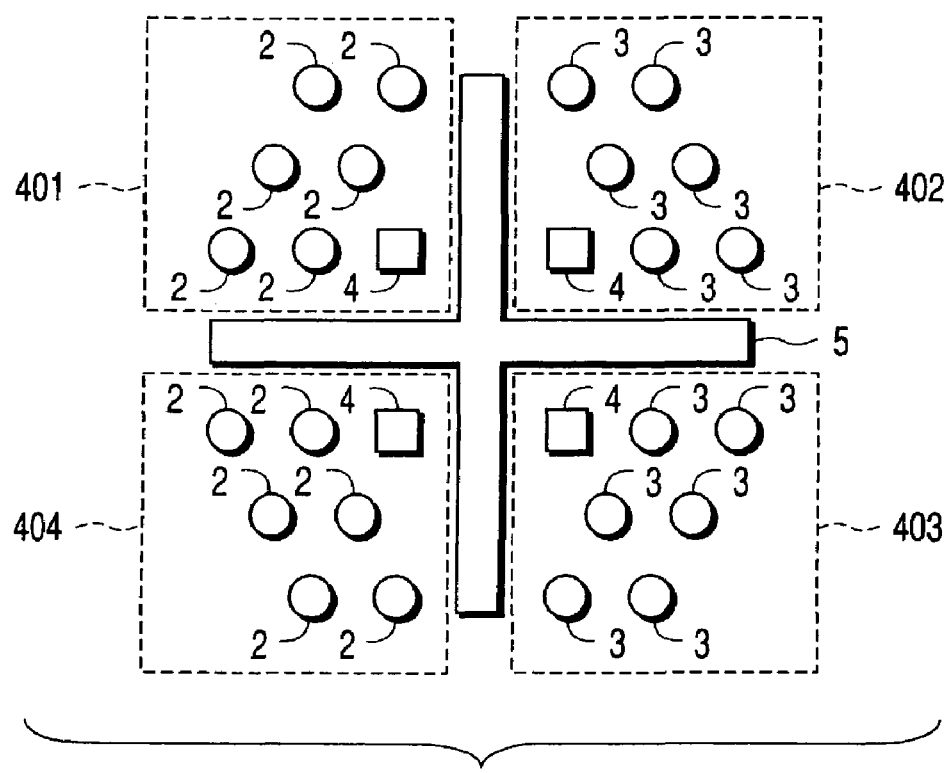
FIG. 14 is a top view of an electrode structure including the detecting electrode and the comparison electrode according to the embodiment.

FIG. 14 is a more specific electrode structural example configured on the basis of the electrode structure of FIG. 13. As shown in FIG. 14, the structures of the counter electrode 4 and the reference electrode 5 are common to those of FIG. 13. In the case of this FIG. 14, at each of four regions 401 through 404 partitioned by the reference electrode 5, a plurality of detecting electrodes 2 are disposed, or a plurality of comparison electrodes 3 are disposed. More specifically, a plurality of detecting electrodes 2 are disposed at the regions 401 and 404 which are adjacent to one another, and a plurality of comparison electrodes 3 are disposed at the regions 402 and 403 which are adjacent to one another. Both of the detecting electrodes 2 and the comparison electrodes 3, which have the same interval from the reference electrode 5, are objects of subtraction. Note that the detecting electrodes 2 may be disposed in at least one of the four regions 401 through 404, and the comparison electrodes 3 may be disposed in at least one region. Accordingly, the detecting electrodes 2 may be disposed at three regions, or the detecting electrodes 2 may be disposed at only one region. Further, a case is shown in which one counter electrode 4 for each region, namely, four counter electrodes 4 in total, are disposed. However, two or more counter electrodes 4 may be disposed at each region. In addition, the detecting electrodes 2 and the comparison electrodes 3 may be disposed so as to be mixed at one region.

The electrode arrangements of FIG. 3 to FIG. 14 shown above are examples, and the shape, the size, the positional relationship, and the like of each electrode can be varied. The electrode structures shown in FIG. 3 to FIG. 14 can be disposed at one semiconductor or a substrate of glass or the like. Accordingly, the detecting electrodes 2 and the comparison electrodes 3 are disposed in the same substrate. The detecting electrode 2 may be one or plural. The comparison electrode 3 may be one or plural. The comparison electrode 3, which is an object of subtraction with respect to the detecting electrode 2, may be one or plural. Further the detecting electrode 2, which is an object of subtraction with respect to the comparison electrode 3, may be one or plural. Of course, the respective electrodes may be disposed on another substrate.

Figure 15:
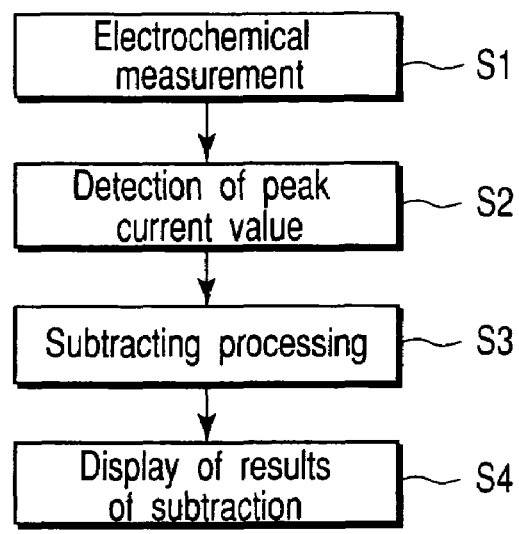
FIG. 15 is a flowchart of operation of the base sequence detecting device according to the embodiment.

Next, operation of the base sequence detecting device described above will be described along the flowchart of FIG. 15.

First, the detecting electrode 2 and the comparison electrode 3 are disposed in the electrochemical cell 1, and a sample (analyte solution) containing a nucleic acid which is the object of inspection is filled in the cell 1. Further, the cell 1 is maintained at a predetermined temperature, and a hybridization reaction between the sample and a target-complementary nucleic acid probe immobilized to the detecting electrode 2 is promoted. After the hybridization reaction is completed, the sample is sent out from the interior of the cell 1, and after it is filled with a buffer agent, the interior of the cell 1 is filled with an intercalating agent. A predetermined voltage is applied, under the feedback of voltage by the reference electrode 5, between the detecting electrode 2 and the comparison electrode 3 in the cell 1 in which the intercalating agent is filled and the counter electrode 4. Thus, electrochemical measurement is carried out by the potentiostats 40 and 50 in parallel at the detecting electrode 2 and the comparison electrode 3 (s1).

Next, peak current values of the current values from the detecting electrode 2 and the comparison electrode 3 obtained by the electrochemical measurement are detected (s2). The detection of the peak current value is carried out in parallel at both of the detecting electrode 2 and the comparison electrode 3. The detection of the peak current values is executed at signal processing units 60 and 70. The signal processing units 60 and 70 extract the peak values of the current waveforms obtained from the potentiostats 40 and 50 or of the voltage waveforms in which the current waveforms are current-voltage converted. Note that the obtained peak current values may be A/D converted, or may be obtained after carrying out a statistical processing such as a mean value calculation of a plurality of detecting electrodes 2 or a plurality of comparison electrodes 3, or the like. The obtained peak current values are outputted to the subtracter 80.

The subtracter 80 subtracts the peak current value for the comparison electrode 3 from the peak current value for the detecting electrode 2 (s3). The peak current value for the detecting electrode 2 is obtained on the basis of a current in which a probe current caused by the intercalating agent molecules interacting with the target-complementary nucleic acid probe and a background current detected as unintended noise are added. In the background current, a current value caused by the intercalating agent molecules interacting with the surface of the detecting electrode 2, and a current value caused by the intercalating agent molecules interacting with the spacer member 22 connecting the nucleic acid probe portion and the surface of the substrate, are included.

The peak current value for the comparison electrode 3 is obtained on the basis of background current detected as unintended noise. Accordingly, by subtraction, the current value due to the background current can be subtracted, and the current due to the probe can be detected.

The subtracter 80 outputs the results of subtraction to the computer 90. The computer 90 displays the results of subtraction on the display device 93. An operator can specify the base sequence included in the sample by the displayed the results of subtraction. Of course, there is provided a determining circuit which carries out determination on the presence/absence of a base sequence included in the sample or the like on the basis of the results of subtraction, and the results of determination may be displayed on the display device 93.

In this way, in accordance with the present embodiment, in addition to a conventional gene detecting electrode as the detecting electrode 2, an electrode which can detect only background current is provided as the comparison electrode 3. After current values at the both electrodes 2, 3 are detected, the current value of the comparison electrode 3 is subtracted from the current value of the detecting electrode 2 by computing on a integrated circuit on the substrate, and it is possible to detect only the current value derived from the target gene from which background current is removed. Because the blocking molecules are formed so as to cover the surfaces of the detecting electrode 2 and the comparison electrode 3, effects of the background current due to interaction of the surfaces of the electrodes and the intercalating agent can be decreased. Further, by using straight chain organic molecules as the spacer member, the background current caused by the spacer can be greatly decreased. Accordingly, even if a probe is not provided at the comparison electrode 3, hardly any difference in the background current due to the presence/absence of a spacer arises. Accordingly, the trouble of immobilizing the spacer and the probe can be eliminated.

In a conventional current detecting type gene detecting method, it was difficult to extract only the current value derived from the target gene and to analyze it. In particular, at the time of discriminating a single base polymorphic, the current value increased due to a nonspecifically hybridized gene, and it was difficult to discriminate it from the background current. However, in accordance with the present embodiment, such a problem can be solved.

The present invention is not limited to the above-described embodiments.

As the probe immobilized to the detecting electrode 2, a probe having a target-complementary base sequence, which is a base sequence complementary with the target base sequence, is used. However, it is not limited to this. For example, a probe (hereinafter called a target semi-complementary nucleic acid probe) may be used, which has a single base or several base sequences different from the target-complementary base sequence and in which the complementation with the target base sequence is lower than that of the target-complementary base sequence. Further, both a target-complementary nucleic acid probe and a target semi-complementary nucleic acid probe may be immobilized to the detecting electrode and used.

Further, in the above-described embodiment, an example is shown in which the surface of the comparison electrode 3 is covered with the blocking molecules 31 and the spacer and the probe are not provided. However, it is not limited to this. FIG. 16 is a diagram showing a modified example of the comparison electrode 3 shown in FIG. 2B. At a comparison electrode 300 according to the modified example, an end of a spacer member 301 comprised of straight chain organic molecules is immobilized via blocking molecules 31. The spacer member 301 is comprised of the same material as that of the spacer member 22 provided at the detecting electrode 2.

A dummy probe 302 is immobilized to the other end of the spacer member 301. The dummy probe 302 is a probe comprising nucleic acid which does not have a base sequence complementary to the target nucleic acid sequence and has a noncomplementary base sequence.

In this way, the probe can also be immobilized to the comparison electrode 3 side via the spacer. In accordance therewith, background current caused by the spacer member 22 at the detecting electrode 2 side can be subtracted by the current at the comparison electrode 3 side.

Further, an example is shown in which, at the detecting electrode 2 side, the target-complementary nucleic acid probe 23 is immobilized to the detecting electrode 2 via the spacer member 22. However, it is not limited to this. For example, as shown in FIG. 22A and FIG. 22B, the target-complementary nucleic acid probe 23 may be immobilized to the detecting electrode 2 not via the spacer member 22.

Although not particularly shown in FIG. 1, the computer 90 may automatically control the respective circuits formed on the semiconductor substrate 101. In this case, the computer 90 outputs control instructions for controlling operations of the potentiostats 40, 50, the signal processing units 60, 70, and the subtracter 80 via a communication interface 91. The respective circuits operate on the basis of the received control instructions, and transmit the results of operation or the results of computation to the computer 90. In accordance therewith, detection of a base sequence can be automated. Further, in FIG. 1, there is shown a case in which the signal processing units 60, 70 and the subtracter 80 are provided at the semiconductor substrate 101. However, the same functions as these may be realized at the computer 90 side. In this case, the output signals of the potentiostats 40 and 50 are transmitted to the computer 90, and signal processing and subtraction processing are executed at the computer 90 side.

As described above, the present invention can precisely carry out detection of current based on interaction with a target base sequence.

EXAMPLES

Hereinafter, more specific Examples of the base sequence detecting device in accordance with the present invention will be described.

In these Examples, the Example of the above-described present embodiment and a Conventional Example for comparing with the Example will be described.

Conventional Example

In this Conventional Example, detection of a nucleic acid was carried out without using the comparison electrode 3. As the detecting electrodes 2, three Au electrodes of detecting electrodes 201, 202, and 203 were used. As the sample nucleic acid, the promoter region of M×A protein having SEQ ID No: 1 was used.

(1) Immobilization of Nucleic Acid Probe to Surface of Au Electrode

The aforementioned sample nucleic acid is the target nucleic acid. The detecting electrode 201 is immersed in a solution containing 10 µM of a single chain nucleic acid probe as a complementary sequence 2 which is complementary to the probe having SEQ ID No: 1 of the target nucleic acid for one hour. In accordance therewith, immobilization of a target-complementary nucleic acid probe 211 to the detecting electrode 201 was carried out. In the same way, single chain nucleic acid probes (hereinafter called target semi-complementary nucleic acid probes 212, 213) having sequences 3, 4 different by a single base from the base sequence complementary to the target nucleic acid, were respectively immobilized to the detecting electrodes 202 and 203. These single chain nucleic acid probes 211 to 213 are respectively immobilized to the detecting electrodes 201 to 203 via a spacer comprising 20 bases (cytosine). Next, the detecting electrodes 201 to 203 were immersed in 1 mM of a mercapto hexanol aqueous solution, and thereby the portions in which the target-complementary nucleic acid probe 211 or the target semi-complementary nucleic acid probes 212, and 213 were not immobilized was blocked.

(2) Detection of Sample Nucleic Acid by Using the Nucleic Acid Probe Immobilized Surface The sample nucleic acid was amplified by PCR after being extracted. The detecting electrodes 201 to 203 prepared in (1) were immersed in 2×SSC solution containing the sample nucleic acid and incubated for 60 minutes at 35° C., and thereby an annealing reaction was carried out. Thereafter, cleaning was carried out with 0.2×SSC solution. Moreover, after the detecting electrodes 201 to 203 and the comparison electrode 3 were immersed for 15 minutes in solution containing 50 µM of Hoechst 33258 solution which was the intercalating agent, the oxidation current response of the Hoechst 33258 molecules was measured. The results of the current measurement are shown in FIG. 17. As compared with the detecting electrode 201, the current values of the detecting electrodes 202 and 203 are low, however, it cannot be distinguished from background current.

Example 1

In this Example 1, detection of a nucleic acid in the same way as in the Conventional Example was carried out by using the comparison electrode 3. As the detecting electrodes 2, three Au electrodes, i.e., detecting electrodes 201, 202, and 203, were used. As the sample nucleic acid, the promoter region of M×A protein having SEQ ID No: 1 was used.

(1) Immobilization of Nucleic Acid Probe to Surface of Au Electrode

The aforementioned sample nucleic acid is the target nucleic acid. The detecting electrode 201 was immersed for one hour in a solution containing 10 µM of a single chain nucleic acid probe having sequence 2 complementary with the target nucleic acid, and thereby immobilization of the target-complementary nucleic acid probe 211 was carried out. In the same way, single chain target semi-complementary nucleic acid probes having sequences 3, 4 different by one base from sequence 2, were respectively immobilized to detecting electrodes 202 and 203. Moreover, a single chain nucleic acid probe (hereinafter called target semi-complementary nucleic acid probe) having sequence 5 which is noncomplementary to sequence 2, was immobilized to the comparison electrode 3. The single chain nucleic acid probes are immobilized to the electrodes via a spacer member comprising 20 bases (cytosine). Next, the detecting electrodes 201 to 203 and the comparison electrode 3 were immersed in a 1 mM mercapto hexanol aqueous solution, and then the portions where the nucleic acid probes were not immobilized were blocked.

(2) Detection of Sample Nucleic Acid by Using Nucleic Acid Probe Immobilized Surface The sample nucleic acid was amplified by PCR after being extracted. The detecting electrodes 201 to 203 and the comparison electrode 3 prepared in (1) were immersed in 2×SSC solution containing the sample nucleic acid and incubated at 35° C. for 60 minutes, and thereby an annealing reaction was carried out. Thereafter, cleaning was carried out with 0.2×SSC solution. Moreover, after the detecting electrodes 201 to 203 and the comparison electrode 3 were immersed for 15 minutes in a solution containing 50 µM of Hoechst 33258 solution which is the intercalating agent, the oxidation current response of the Hoechst 33258 molecules was measured. After the current measurement, the background current was removed by a subtracter. The results after removal are shown in FIG. 18. It is shown that, at the detecting electrode 202, there is hardly any current value derived from the gene which is the object of detection, and the difference of the one base can be clearly distinguished. On the other hand, it is found that, at the detecting electrode 203, the gene which is the object is non-specifically hybridized. In accordance with this Example 1, it was clear that only the current derived from the object gene can be extracted by carrying out gene detection by using the comparison electrode 3.

Example 2

In Conventional Example 1 and Example 1, as the spacer member of the nucleic acid probe, a base sequence which is easy to interact with intercalating agent molecules was used. Therefore, the nucleic acid probe was immobilized to the comparison electrode 3 also. In this Example 2, as the spacer member of the nucleic acid probe, ethylene glycol molecules, which do not interact with the intercalating agent molecules, were used. As the sample nucleic acid, the promoter region of MxA protein having SEQ ID No: 1 was used.

(1) Immobilization of Nucleic Acid Probe to Surface of Au Electrode

The aforementioned sample nucleic acid is the target nucleic acid. The detecting electrode 201 was immersed for one hour in a solution containing 10 µM of a single chain complementary nucleic acid probe 211 having sequence 2 complementary with the target nucleic acid, and thereby immobilization of the nucleic acid probe was carried out. In the same way, single chain target semi-complementary nucleic acid probes 212 and 213 having sequences 3, 4 different by one base from the target nucleic acid were immobilized to detecting electrodes 202 and 203. Immobilization of a single chain nucleic acid probe to the comparison electrode 3 is not carried out. The single chain nucleic acid probes 211 to 213 were fixed to the respective electrodes via a spacer comprising 30 ethylene glycol molecules. Next, the detecting electrodes 201 to 203 and the comparison electrode 3 were immersed in a 1 mM mercapto hexanol aqueous solution, and then the portions where the nucleic acid probes were not immobilized were blocked.

Figure 19:
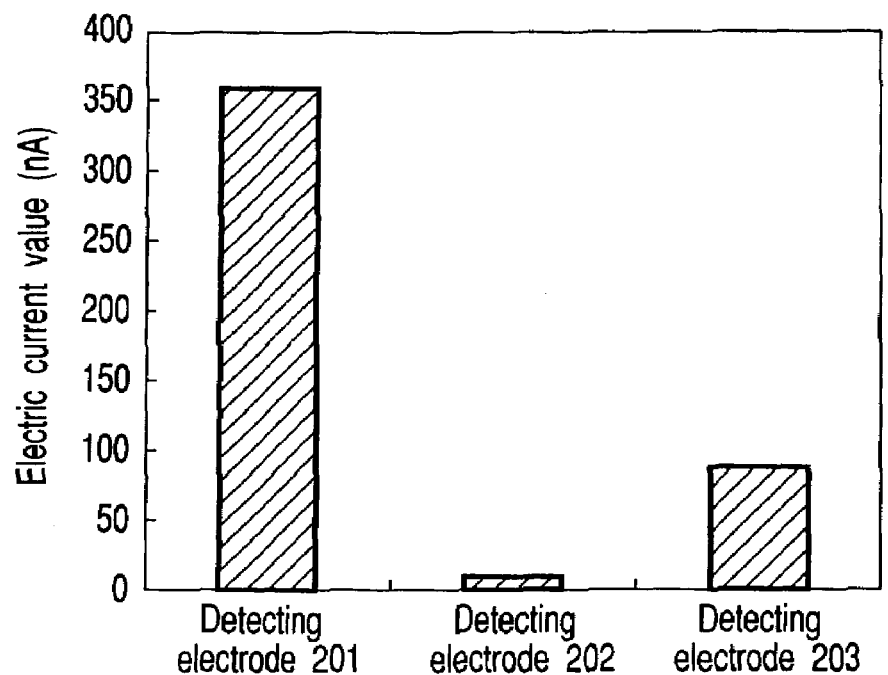
FIG. 19 is a graph showing results of current measurement of a base sequence detecting device in which ethylene glycol molecules are used as a spacer member.

(2) Detection of Sample Nucleic Acid by Using Nucleic Acid Probes Immobilized Surface The sample nucleic acid was amplified by PCR after being extracted. The detecting electrodes 201, 202 and the comparison electrode 3 prepared in (1) were immersed in 2×SSC solution containing the sample nucleic acid and incubated at 35° C. for 60 minutes, an annealing reaction was carried out. Thereafter, cleaning was carried out with 0.2×SSC solution. Moreover, after the detecting electrodes 201, 202 and the comparison electrode 3 were immersed for 15 minutes in a solution containing 50 µM of Hoechst 33258 solution which is the intercalating agent, the oxidation current response of the Hoechst 33258 molecules was measured. After the current measurement, the background current was removed by a subtracter. The results after the removal are shown in FIG. 19. It is shown that, at the detecting electrode 202, there is hardly any current value derived from the gene which is the object of detection, and the difference of the one base can be clearly distinguished. On the other hand, it is found that, at the detecting electrode 203, the gene which is the object is non-specifically hybridized. In accordance with this Example 2, it was clear that, by using ethylene glycol as the spacer of the nucleic acid probe immobilized to the detecting electrode 2, it could be comprised of only by blocking molecules without immobilizing a nucleic acid probe to the comparison electrode 3.

16

Example 3

In this Example 3, blocking molecules other than those of the Conventional Example and Examples 1 and 2 were used. As the spacer member of the nucleic acid probe, a molecule in which five ethylene glycol molecules were bound was used. As the sample nucleic acid, the promoter region of MxA protein having SEQ ID No: 1 was used.

(1) Immobilization of Nucleic Acid Probe to Surface of Au Electrode

The aforementioned sample nucleic acid is a target nucleic acid. The detecting electrode 201 was immersed for one hour in a solution containing 10 µM of a single chain target-complementary nucleic acid probe 211 having sequence 2 complementary with the sample nucleic acid, and thereby immobilization of the nucleic acid probe was carried out. In the same way, single chain target semi-complementary nucleic acid probes 212 and 213 having sequences 3, 4 different by one base from the sample nucleic acid were immobilized to the detecting electrodes 202 and 203. Fixing of the single chain nucleic acid probe to the comparison electrode 3 was not carried out. The single chain nucleic acid probes 211 to 213 were immobilized to the electrodes via a spacer comprising 30 ethylene glycol molecules. Next, the detecting electrodes 201 to 203 and the comparison electrode 3 were immersed in 1 mM of a mercapto octanol aqueous solution, and then the portions where the nucleic acid probes were not fixed were blocked.

(2) Detection of Sample Nucleic Acid by Using the Nucleic Acid Probe Immobilized Surface.

Figure 20:
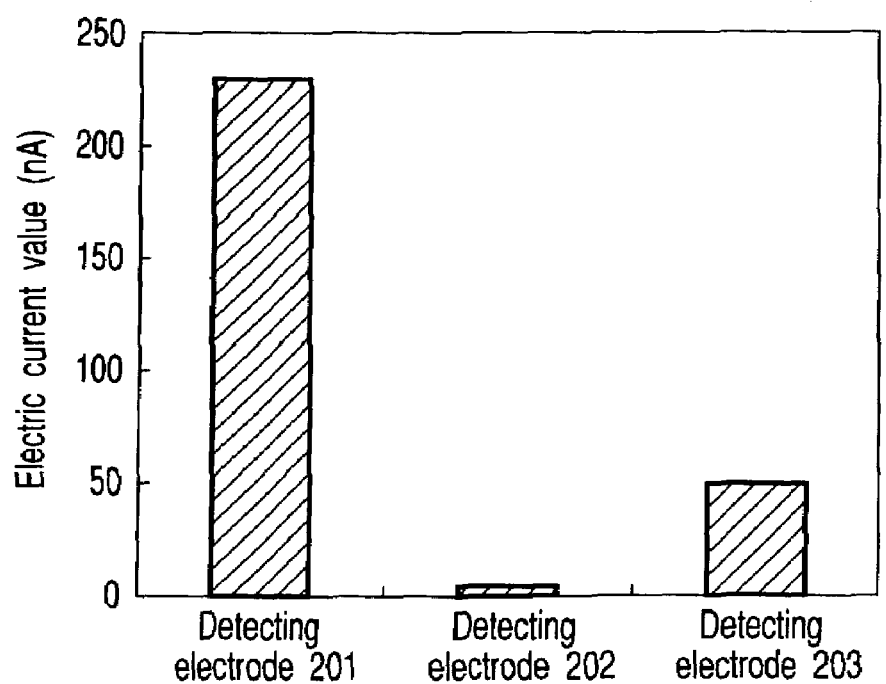
FIG. 20 is a graph showing results of current measurement of a base sequence detecting device in which mercapto octanol is used as blocking molecules.

The sample nucleic acid was amplified by PCR after being extracted. The detecting electrodes 201 to 203 and the comparison electrode 3 prepared in (1) were immersed in 2×SSC solution containing the sample nucleic acid and incubated at 35° C. for 60 minutes, an annealing reaction was carried out. Thereafter, cleaning was carried out with 0.2×SSC solution. Moreover, after the detecting electrodes 201 to 203 and the comparison electrode 3 were immersed for 15 minutes in a solution containing 50 µM of Hoechst 33258 solution which is the intercalating agent, the oxidation current response of the Hoechst 33258 molecules was measured. After the current measurement, the background current was removed by a subtracter. The results after removal are shown in FIG. 20. It is shown that, at the detecting electrode 202, there is hardly any current value derived from the gene which is the object of detection, and the difference of the one base can be clearly distinguished. On the other hand, it is found that, at the detecting electrode 203, the object gene is non-specifically hybridized.

Example 4

In this Example 4, as the spacer member of the nucleic acid probe, straight chain alkane molecules were used. As the sample nucleic acid, the promoter region of MxA protein having SEQ ID No: 1 was used.

(1) Immobilization of Nucleic Acid Probe to Surface of Au Electrode

The aforementioned sample nucleic acid is the target nucleic acid. The detecting electrode 201 was immersed for one hour in a solution containing 10 µM of the single chain target-complementary nucleic acid probe 211 having sequence 2 complementary with the sample nucleic acid, and thereby immobilization of the nucleic acid probe 211 to the detecting electrode 201 was carried out. In the same way, the single chain target semi-complementary nucleic acid probes 212 and 213 having sequences 3, 4 different by one base from the sample nucleic acid were immobilized to the detecting electrodes 202 and 203. Fixing of a single chain nucleic acid probe to the comparison electrode 3 is not carried out. The single chain complementary nucleic acid probe 211 and the target semi-complementary nucleic acid probes 212 and 213 were fixed to the electrodes via a spacer comprising straight chain alkane molecules having 96 carbons. Next, the detecting electrodes 201 to 203 and the comparison electrode 3 were immersed in a 1 mM mercapto hexanol aqueous solution, and then the portions where the nucleic acid probes were not immobilized were blocked.

(2) Detection of Sample Nucleic Acid by Using the Nucleic Acid Probes Immobilized Surface The sample nucleic acid was amplified by PCR after being extracted. The detecting electrodes 201 to 203 and the comparison electrode 3 prepared in (1) were immersed in 2×SSC solution containing the sample nucleic acid and incubated at 35° C. for 60 minutes, and thereby an annealing reaction was carried out. Thereafter, cleaning was carried out with 0.2×SSC solution. Moreover, after the detecting electrodes 201 to 203 and the comparison electrode 3 were immersed for 15 minutes in a solution containing 50 μM of Hoechst 33258 solution which is the intercalating agent, the oxidation current response of the Hoechst 33258 molecules was measured. After the current measurement, the background current was removed by a subtracter. The results after removal are shown in FIG. 21. It is shown that, at the detecting electrode 202, there is hardly current value derived from the gene which is the object of detection, and the difference of the one base can be clearly distinguished. In accordance with the Example 4, it was clear that, by using straight chain alkane molecules as the spacer of the nucleic acid probe, it can be configured by only blocking molecules without immobilizing a nucleic acid probe to the comparison electrode 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

As described above, the present invention is advantageous in the technical field of detecting electrodes for detecting base sequences, the technical field of detecting devices for detecting base sequences, and the technical field of detecting methods for detecting base sequences.

The invention claimed is:

1. A base sequence detecting electrode comprising:
a conductive detecting electrode;
first blocking molecules formed so as to cover a surface of the detecting electrode, the first blocking molecules decreasing adsorption of an intercalating agent to the surface of the detecting electrode;
a target-complementary probe immobilized to the detecting electrode, the target-complementary probe including a base sequence complementary to a target base sequence which is an object of detection;
a conductive comparison electrode;
second blocking molecules formed so as to cover a surface of the comparison electrode, the second blocking molecules decreasing adsorption of an intercalating agent to the surface of the comparison electrode; and
a dummy probe immobilized to the comparison electrode via a first spacer member including straight chain organic molecules, the dummy probe including a base sequence noncomplementary to the target base sequence which is the object of detection,
wherein the detecting electrode is configured to detect a probe current caused by interaction between the intercalating agent and the target-complementary probe hybridized with the target, and the comparison electrode is configured to detect a background current.

2. The base sequence detecting electrode according to claim 1, wherein the target-complementary probe is fixed to the detecting electrode via a second spacer member comprising straight chain organic molecules.

3. The base sequence detecting device according to claim 1, further comprising:
a counter electrode which applies a predetermined voltage between the counter electrode and the detecting electrode; and a first reference electrode to set voltage to be detected to the counter electrode.

4. The base sequence detecting electrode according to claim 3, wherein the counter electrode to apply a predetermined voltage between the counter electrode and the detecting electrode, and between the counter electrode and the comparison electrode.

5. The base sequence detecting device according to claim 1, wherein the first blocking molecules adsorb to the surface of the detecting electrode via one of a thiol group and an amino group to prepare an amino group self-organizing monomolecular film.

6. The base sequence detecting electrode according to claim 1, wherein the straight chain organic molecules include one of straight chain alkane, alkene, alkyne, ether, ester, and ketones, and include a molecule in which several molecules of straight chain alkane, alkene, alkyne, ether, ester, and ketones are connected in a chain via atoms including one of oxygen, nitrogen, and sulphur.

7. The base sequence detecting device comprising:
a conductive detecting electrode;
first blocking molecules formed so as to cover a surface of the detecting electrode, the first blocking molecules decreasing adsorption of an intercalating agent to the surface of the detecting electrode;
a target-complementary probe immobilized to the detecting electrode, the target-complementary probe including a base sequence complementary to a target base sequence which is an object of detection;
a conductive comparison electrode;
second blocking molecules formed so as to cover a surface of the comparison electrode, the second blocking molecules decreasing adsorption of an intercalating agent to the surface of the comparison electrode;
a subtracter which subtracts an electrochemical signal detected at the comparison electrode from an electrochemical signal detected at the detecting electrode; and
a dummy probe immobilized to the comparison electrode via a first spacer member including straight chain organic molecules, the dummy probe including a base sequence noncomplementary to the target base sequence which is the object of detection,
wherein the detecting electrode is configured to detect a probe current caused by interaction between the intercalating agent and the target-complementary probe hybridized with the target, and the comparison electrode is configured to detect a background current.

8. The base sequence detecting device according to claim 7, wherein the target-complementary probe is fixed to the detecting electrode via a second spacer member comprising straight chain organic molecules.

9. The base sequence detecting device according to claim 7, further comprising:
a first potentiostat to detect an electrochemical signal from the detecting electrode by applying a predetermined voltage between the detecting electrode and a first counter electrode disposed so as to face the detecting electrode;
a first signal processing unit which signal-processes an output of the first potentiostat and outputs it to the subtracter;
a second potentiostat which detects an electrochemical signal from the comparison electrode by applying a predetermined voltage between the comparison electrode and a second counter electrode disposed so as to face the comparison electrode; and
a second signal processing unit which signal-processes an output of the second potentiostat and outputs it to the subtracter.

10. The base sequence detecting device according to claim 7, further comprising a display device which displays results of subtraction of the subtracter.

11. The base sequence detecting device according to claim 10, wherein the detecting electrode, the comparison electrode, and the subtracter are formed on the same substrate, and the subtracter and the display device are connected with each other via a computer by means of a signal line.

12. The base sequence detecting device according to claim 7, further comprising:

a detecting electrode side 3-electrode system which comprises: the detecting electrode; a first counter electrode to apply a predetermined voltage between the first counter electrode and the detecting electrode, the first counter electrode being disposed so as to be apart by a first distance from the detecting electrode; and a first reference electrode to set voltage to be detected to the first counter electrode, the first reference electrode being disposed so as to be apart by a second distance from the detecting electrode; and a comparison electrode side 3-electrode system which comprises: the comparison electrode; a second counter electrode to apply a predetermined voltage between the second counter electrode and the comparison electrode, the second counter electrode being disposed so as to be apart by a first distance from the comparison electrode; and a second reference electrode to set voltage to be detected to the second counter electrode, the second reference electrode being disposed so as to be apart by a second distance from the detecting electrode, wherein a plurality of sets of the detecting electrode side 3-electrode system and the comparison electrode side 3-electrode system are disposed in a matrix manner.

13. The base sequence detecting device according to claim 7, further comprising:

a detecting electrode group in which a plurality of the detecting electrodes are disposed at equal intervals in a first direction;

a reference electrode which is disposed so as to be apart by a predetermined distance from the detecting electrode group, and has a longitudinal direction in the first direction;

a comparison electrode group which is disposed so as to be apart by a predetermined distance from the reference electrode, and in which a plurality of the comparison electrodes are disposed at equal intervals in the first direction; and a counter electrode to apply a predetermined voltage between each of the detecting electrodes and each of the comparison electrodes, the counter electrode being disposed so as to be apart by a predetermined distance from the comparison electrode group, and having a longitudinal direction in the first direction.

14. The base sequence detecting device according to claim 7, further comprising:

a detecting electrode group in which a plurality of detecting the electrodes are disposed at equal intervals in a first direction;

a comparison electrode group in which a plurality of the comparison electrodes are disposed at equal intervals in the first direction;

a counter electrode to apply a predetermined voltage to each of the detecting electrodes, the counter electrode being disposed so as to be apart by a predetermined distance from the detecting electrode group and the comparison electrode group, and having a longitudinal direction in the first direction; and a reference electrode to negatively feed back a voltage to be detected to the counter electrode, the reference electrode being disposed so as to be apart by a predetermined distance from the detecting electrode group, the comparison electrode group, and the counter electrode, and having a longitudinal direction in a second direction substantially perpendicular to the first direction.

15. The base sequence detecting device according to claim 7, further comprising:

a detecting electrode side electrode group which comprises the detecting electrode and a first reference electrode disposed so as to be apart by a first distance from the detecting electrode;

a comparison electrode side electrode group which comprises the comparison electrode and a second reference electrode disposed so as to be apart by the first distance from the comparison electrode; and a counter electrode to apply a predetermined voltage between each of the detecting electrodes and each of the comparison electrodes, the counter electrode having a longitudinal direction in a first direction, wherein the detecting electrode side electrode group and the comparison electrode side electrode group are disposed in a matrix manner in the first direction and a second direction different from the first direction.

16. The base sequence detecting device according to claim 7, further comprising:

a circular counter electrode to apply a predetermined voltage to the detecting electrode and the comparison electrode; and a ring-shaped reference electrode disposed so as to be apart by a predetermined distance from the counter electrode so that the ring-shaped reference electrode encircles the counter electrode, wherein a plurality of the detecting electrodes and a plurality of the comparison electrodes are alternately disposed on a circumference whose center is the counter electrode.

17. The base sequence detecting device according to claim 7, further comprising:

a reference electrode which comprises a first member having a longitudinal direction in a first direction, and a second member having a longitudinal direction in a direction substantially perpendicular to the first direction and intersecting the first member at a first intersection; and four counter electrodes disposed so as to be apart by a first distance from the first intersection at each of four regions partitioned by the reference electrode, wherein a plurality of the detecting electrodes are disposed in at least one of the four regions so as to be apart from the first intersection by a distance longer than the first distance, and a plurality of the comparison electrodes are disposed in at least one of the four regions so as to be apart from the first intersection by a distance longer than the first distance.

18. The base sequence detecting device according to claim 17, wherein the comparison electrode is disposed in a region where the detecting electrode is not disposed among the four regions, and the detecting electrode is disposed in a region where the comparison electrode is not disposed among the four regions.

19. The base sequence detecting device according to claim 7, further comprising:
   a counter electrode which applies a predetermined voltage between the counter electrode and the detecting electrode; and a first reference electrode to set voltage to be detected to the counter electrode.

20. The base sequence detecting electrode according to claim 19, wherein the counter electrode to apply a predetermined voltage between the counter electrode and the detecting electrode, and between the counter electrode and the comparison electrode.

21. The base sequence detecting device according to claim 7, wherein the first blocking molecules adsorb to the surface of the detecting electrode via one of a thiol group and an amino group to prepare an amino group self-organizing monomolecular film.

22. The base sequence detecting device according to claim 7, wherein the straight chain organic molecules include one of straight chain alkane, alkene, alkyne, ether, ester, and ketones, and include a molecule in which several molecules of straight chain alkane, alkene, alkyne, ether, ester, and ketones are connected in a chain via atoms including one of oxygen, nitrogen, and sulphur.

* * * * *